United States Patent
Castaldi et al.

(10) Patent No.: US 6,696,591 B1
(45) Date of Patent: Feb. 24, 2004

(54) PROCESS FOR OBTAINING (NITROXYMETHYL)PHENYL ESTERS OF SALICYLIC ACID DERIVATIVES

(75) Inventors: Graziano Castaldi, Novara (IT); Erminio Oldani, Milan (IT); Gabriele Razzetti, Milan (IT); Francesca Benedini, Milan (IT)

(73) Assignee: Nicox S.A., Paris (FR)

( * ) Notice: Subject to any disclaimer, the term of this patent is extended or adjusted under 35 U.S.C. 154(b) by 10 days.

(21) Appl. No.: 10/019,316

(22) PCT Filed: Jun. 21, 2000

(86) PCT No.: PCT/EP00/05722

§ 371 (c)(1), (2), (4) Date: Jan. 9, 2002

(87) PCT Pub. No.: WO01/04082

PCT Pub. Date: Jan. 18, 2001

(30) Foreign Application Priority Data

Jul. 9, 1999 (IT) .......................................... MI99A1517

(51) Int. Cl.[7] .............................................. C07C 203/04
(52) U.S. Cl. ....................................... 558/482; 548/577
(58) Field of Search ........................................ 558/482

(56) References Cited

FOREIGN PATENT DOCUMENTS

| WO | WO 97/16405 | 5/1997 |
|---|---|---|
| WO | WO 00/44705 | 8/2000 |

OTHER PUBLICATIONS

Olah et al.; "Nitration: Methods and Mechanisms", VCH ed., 1984, p. 269.

Albright & Hanson; "Industrial and Laboratory Nitrations", ACS publ., 1976, p. 156.

Primary Examiner—Alan L. Rotman
Assistant Examiner—Kamal Saeed
(74) Attorney, Agent, or Firm—Arent Fox Kintner Plotkin & Kahn

(57) ABSTRACT

A process for obtaining (nitroxymethyl)phenyl esters of salicylic acid derivatives of formula (I) wherein $R_1$ is the $OCOR_3$ group characterized in that it comprises the following steps: a) reaction of a halide of a salicylic acid derivative with hydroxybenzylacohol in the presence of a base: b) nutration of the obtained product in anhydrous conditions by a mixture of nitric acid with a different inorganic acid, or an organic acid, or an anhydride of one or two organic acids: c) recovery of the final product.

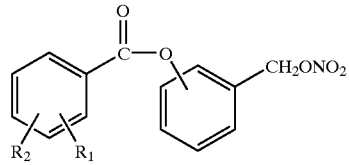

(I)

9 Claims, No Drawings

PROCESS FOR OBTAINING (NITROXYMETHYL)PHENYL ESTERS OF SALICYLIC ACID DERIVATIVES

The present invention relates to a process for obtaining (nitroxymethyl)phenyl esters of salicylic acid derivatives.

It is known in the prior art that the (nitroxymethyl)phenyl esters of the salicylic acid derivatives can be prepared by various synthesis processes. In the patent application WO 97/16405 the reaction of the acyl chloride of the acetylsalicylic acid with (nitroxymethyl)phenol is described. The (nitroxymethyl)phenol is prepared by a synthesis which comprises the following steps:

reaction of the phenol with HBr in organic solvent to obtain (bromomethyl)phenol, and reaction of the (bromomethyl)phenol in organic solvent with $AgNO_3$ with formation of (nitroxymethyl)phenol The process based on the reaction between (nitroxymethyl)phenol and the acyl chloride of the acetylsalicylic acid shows the following drawbacks:

the (bromomethyl)phenol obtained in the first synthesis step is a chemically unstable and irritating compound;

the nitrating agent used in the reaction with (bromomethyl)phenol is a very expensive reactant;

the (nitroxymethyl)phenol is an unstable compound, which can easily decompose in an uncontrollable way; and it must be purified before the reaction with the acetylsalicylic acid chloride, furtherly increasing the production costs and requiring supplementary units in the production plant.

In conclusion the synthesis of above derivatives, by using the intermediate (nitroxymethyl)phenol, is difficult and expensive to be carried out on an industrial scale.

In PCT Patent EP 00/00353 in the name of the Applicant a synthesis process of nitroxy derivatives of formula (I) (see hereunder) is described, by submitting to nitration with $AgNO_3$ (hydroxymethyl)phenyl esters of the acetylsalicylic acid, obtained by reacting the acid chloride with hydroxybenzaldehyde and reducing the aldehydic group to primary alcohol. Also this process, as the above mentioned uses silver nitrate as nitrating agent and therefore it is not much advantageous from an industrial point of view. Besides the process global yields are not high.

By using the teaching of the prior art, it is possible to obtain the salicylic acid nitroxyderivatives of formula (I) (see below) by reacting a (hydroxymethyl)phenyl ester of the acetylsalicylic acid with nitrating reactants based on nitric acid. However under the reaction conditions of the prior art the nitric acid produces undesired reactions, such as for example the nitration of aromatic substrata (ref. "Nitration: Methods and Mechanism", 1984 VCH ed., p. 269) and the oxidation of primary alcohols to aldehydes (ref. "Industrial and Laboratory Nitration" 1976 ACS publ., p. 156).

Therefore also said processes of the prior art are unable to solve the problem of the preparation on industrial scale of the nitroxyderivatives of the salicylic acid as above defined.

The need was felt to prepare nitroxy derivatives of (hydroxymethyl)phenyl esters of the acetylsalicylic acid by a process cheaper than those of the prior art both for the nitrating agent used and for the yields, and substantially without the drawbacks of the prior art.

An object of the present invention is a process for obtaining (nitroxymethyl)phenyl esters of the salicylic acid derivatives, compounds having the following formula (I):

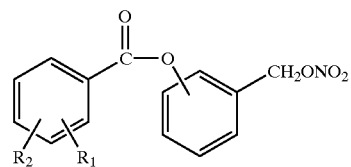

(I)

wherein:

$R_1$ is the $OCOR_3$ group; wherein $R_3$ is methyl, ethyl or linear or branched $C_3$–$C_5$ alkyl, or the residue of a saturated heterocyclic ring having 5 or 6 atoms, containing hetero-atoms independently selected between O and N;

$R_2$ is hydrogen, halogen, linear or branched when possible $C_1$–$C_4$ alkyl, linear or branched when possible $C_1$–$C_4$ alkoxyl; linear or branched when possible $C_1$–$C_4$ perfluoroalkyl, for example trifluoromethyl; mono- or di-($C_1$–$C_4$)alkylamino;

preferably in (I) $R_1$ is acetoxy and is in ortho position with respect to the carboxylic group, $R_2$ is hydrogen; the oxygen of the ester group is bound to the aromatic ring substituted with the (nitroxy)methylene group in ortho, meta or para position with respect to the (nitroxy)methylene group; preferably the position is the meta one;

said process comprising the following steps:

a) reaction of a halide of a salicylic acid derivative of formula (I-A):

(I-A)

wherein Hal=Cl, Br, and K and $R_1$ and $R_2$ have the above indicated meaning, with hydroxybenzylalcohol in the presence of a base, in an organic solvent, or in a mixture of water with a miscible or immiscible organic solvent with water, to give the compound (I-B) having the following formula:

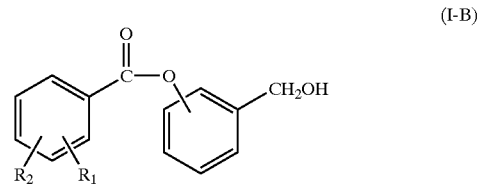

(I-B)

wherein $R_1$ and $R_2$ are as above defined;

b) nitration of the compound (I-B) in anhydrous conditions, in an inert organic solvent, by a mixture formed by steaming nitric acid with an inorganic acid different from nitric acid or with an organic acid, or with the anhydride of one or two organic acids, to give the nitroxyderivative of formula (I).

c) recovery of the final product by adding water to the organic phase, separating the phases, drying and evaporating the organic phase.

In step a) the base can be an inorganic base, such as for example hydroxides, oxides, carbonates and bicarbonates of alkaline metals (sodium, potassium, lithium); or an organic base, for example a tertiary amine, for example aliphatic, cycloaliphatic, heterocyclic, heterocyclic aromatic, such as triethylamina, diisopropyl-ethylamine, N-methylmorpholine, diazaabicyclooctane, etc.

The organic solvent used in step a) can be an organic solvent miscible with water such as $C_1$–$C_4$ aliphatic alcohols, for example methanol, ethanol, isopropanol, n-butanol; or an organic solvent immiscible with water for example aromatic hydrocarbons such as toluene and xylene, chlorinated organic solvents such as methylene chloride, chlorobenzene, other solvents which can be used are aliphatic esters for example of $C_1$–$C_4$ acids with $C_1$–$C_5$ alcohols such as for example ethyl acetate and butyl acetate, etc.: aliphatic and cycloatiphatic ketones, such as $C_3$–$C_{12}$ for example acetone, methylketone, cyclohexanone, etc.

In step a) the reaction is carried out at a temperature in the range −20° C., and +50° C., preferably 0° C.–20° C., by using, with respect to the hydroxybenzylalcohol moles under reaction, an amount by moles of acid halide (I-A) in a ratio between 1 and 2, preferably between 1.2 and 1.5, and an amount by moles of base between 0.1 and 2, preferably between and 2.

The compound I-B) is recovered from the reaction mixture by addition of water and optionally, when the reaction takes place in an aqueous solvent or in a mixture of water with an hydrosoluble organic solvent, by addition of an organic solvent immiscible with water, such as ethyl acetate or dichloromethane, the phases are separated, the organic phase is dried, evaporated and the product is recovered. If necessary, the compound can be purified by crystallization from solvents such as for example n-hexane, n-heptane, ligroin, toluene, methanol, isopropanol, diisopropylether, etc or their mixtures. Generally the yields are higher than 80%.

In step b) the nitration reaction is carried out at a temperature in the range −20° C. and +40° C., preferably from 0° C. to 20° C.; the used amount by moles of nitric acid is in a ratio between 1 and 6, preferably 1 and 3, with respect to the moles of the hydroxyester (I-B); the amount by moles of organic or inorganic acid different from nitric acid, or of anhydride as above defined, is in a ratio comprised between 0.5 and 6, preferably between 1 and 3 with respect to the moles of the compound (I-B).

The inorganic acid different from nitric acid is for example sulphuric acid; the organic acid is for example methansulphonic acid, trifluoromethansulphonic acid, trifluoroacetic acid, trichloroacetic acid, acetic acid; the organic acid anhydride is for example acetic anhydride, trifluoromethansulphonic anhydride, trifluoroacetic anhydride, trichloroacetic anhydride, etc., or mixed anhydrides such as for example trifluoroacetic-trifluoromethansulphonic anhydride, etc.

The inert organic solvent used in step b) is a solvent which has boiling point lower than 200° C. at atmospheric pressure and it can be a chlorinated solvent, such as for example dichloromethane; or a nitroalkane such as for example nitromethane, or an aliphatic or cycloaliphatic ether such as for example methylterbutylether, tetrahydrofuran, etc.; an ester for eaample ethyl acetate; or an aliphatic or aromatic nitrile such as for example acetonitrile, benzonitrile.

The solvent volume is not critical, generally the volume is comprised betwen 1 and 20 times with respect to the amount by weight of hydroxyester (I-B) under reaction.

When the nitration in step b) is carried out in the presence of an organic anhydride as above defined, preferably the anhydride is first mixed with the hydroxyester (I-B) and then the resulting mixture is added to the nitric acid solution in the inert organic solvent.

Preferably the used organic anhydride is acetic anhydride.

In step c) it is possible to recrystallize the obtained compound by using solvents such as for example n-hexane, n-heptane, ligroin, methanol, isopropanol or their mixtures.

The following Examples describe the invention without limiting the scope thereof.

EXAMPLE 1a

Preparation of 3-Hydroxymethylphenyl Ester of the 2-Acetoxybenzoic Acid (Compound I-B) in Admixture Water-organic Solvent 3-hydroxymethylphenol (25.25 g, 0.2 moles) is dissolved in a 5% hydroxide sodium solution (160 ml). To the so obtained solution an acetylsalicylic acid chloride solution (40.4 g, 0.2 moles) in dichloromethane (50 ml) is added at roam temperature, under stirring. The mixture is maintained at room temperature under stirring for 2 hours and then extracted with dichloromethane (2×100 ml). The organic phase is separated, anhydrified with sodium sulphate and the solvent evaporated under vacuum. The residue is crystallized from a mixture of ethyl acetate and hexane. 3-hydroxymethylphenyl ester of the 2-acetoxybenzoic acid (45.8 g, 0.16 moles, yield 80%) is obtained.

M.P.: 79°–81° C. $^1$H NMR($CDCl_3$) δ (ppm): 2.29 (s, 3H); 4.71 (s, 2H); 7.07–8.2 (m, aromatics, 8H).

EXAMPLE 1b

Preparation of 3-Hydroxymethylphenyl Ester of the 2-Acetoxybenzoic Acid (Compound I-B) in Organic Solvent Immiscible With Water 3-hydroxymethylphenol (10 g, 0.08 moles) is dissolved in toluene (50 ml) containing triethylamine (9.8 g, 0.1 moles). To the so obtained solution an acetylsalicylic acid chloride solution (16 g, 0.08 moles) in toluene (50 ml) is added at a temperature of 5°–10° C. under stirring. The mixture is maintained at a temperature in the above mentioned range, under stirring for 2 hours, then poured in water and then extracted with dichloromethane (2×100 ml). The organic phase is separated, washed in sequence with a 25% w/v potassium carbonate solution, with water, with a 3% hydrochloric acid solution and lastly with water again, then anhydrified with sodium sulphate and the solvent evaporated under vacuum. The residue is crystallized from isopropanol. 3-hydroxymethylphenyl ester of the 2-acetoxybenzoic acid (45.8 g, 0.16 moles, yield 80%) is obtained.

M.P.: 79°–80° C. $^1$H NMR($CDCl_3$) δ (pp): 2.29 (s, 3H); 4.71 (s, 2H); 7.07–8.2 (m, aromatics, 8H).

EXAMPLE 1c

Preparation of 3-Hydroxymethylphenyl Ester of the 2-Acetoxybenzoic Acid (Compound I-B) in Organic Solvent Miscible With Water 3-hydroxymethylphenol (10 g, 0.08 moles) is dissolved in acetone (50 ml). In the obtained solution potassium carbonate in powder (22.2 g, 0.16 moles) is suspended. To the suspension an acetylsalicylic acid chloride solution (16 g, 0.08 moles) in acetone (50 ml) is added at a temperature of 5°–10° C. under stirring. The mixture is maintained at a temperature in the above mentioned range, under stirring, for 2 hours, then filtered and the solvent evaporated under vacuum. The residue is crystallized from isopropanol. 3-hydroxymethylphenyl ester of the 2-acetoxy-benzoic acid (21.0 g, 0.07 moles, yield 91%) is obtained.

M.P.: 79°–80° C. $^1$H NMR($CDCl_3$) δ (ppm): 2.29 (s, 3H); 4.71 (s, 2H); 7.07–8.2 (m, aromatics, 8H).

EXAMPLE 2

Preparation of 3-Nitroxymethylphenyl Ester of the 2-Acetoxybenoic Acid by Nitration With Steaming Nitric Acid, in the Presence of Sulphuric Acid, of 3-Hydroxymethylphenyl Ester of the 2-Acetoxybenzoic Acid A solution of steaming nitric acid (3.92 g, 62.2 mmoles, 3 moles with respect to the moles of the hydroxyester I-B) and sulphuric acid 96% (6.10 g, 62.2 mmoles, 3 moles with respect to the moles of the hydroxyester 1-B) in dichloromethane (25 ml) is cooled at 0° C. and added in 1 hour, under stirring and in nitrogen atmosphere, with a 3-hydroxymethylphenyl ester solution of the 2-acetoxybenzoic acid (6 g, 20.7 mmoles) in 25 ml of dichloromethane. The mixture is then diluted with dichloromethane (50 ml) and poured into water and ice (100 g). The organic phase is separated, washed with water, anhydrified with sodium sulphate and the solvent evaporated under vacuum. The residue is crystallized from isopropanol obtaining the 3-nitroxymethylphenyl ester of the 2-acetoxybenzoic acid (5.6 g, 17 mmoles, yield 82%).

M.P.: 61°–62° C. $^1$H NMR(CDCl$_3$) δ (ppm): 2.31 (s, 3H); 5.44 (s, 2H); 7.16–8.22 (m, aromatics, 8H).

EXAMPLES 2a–2f

Example 2 was repeated by varying the moles of nitric acid and of sulphuric acid with respect to the moles of the intermediate 3-hydroxymethylphenyl ester of the 2-acetoxybenzoic acid (I-B). In the following Table 1 the molar ratios of the used reactants with respect to the compound I-B and the relative per cent ratio between the 3-nitroxymethylphenyl ester of the 2-acetoxybenzoic acid (I), the 3-(formyl)phenyl ester of the 2-acetoxybenzoic acid (I-B1) are reported, considering, when present, also the starting compound (I-B).

The Table shows that the highest yield is obtained by using the molar ratio nitric acid/compound (I-B) equal to 3 and sulphuric acid/compound (I-B) equal to 1.5.

TABLE 1

| Example | Moles HNO$_3$/I-B | Eq. H$_2$SO$_4$/I-B | Moles H$_2$SO$_4$/I-B | Relative Ratio % (I) | (I-B) | (I-B1) |
|---|---|---|---|---|---|---|
| a | 2 | 0 | 0 | 5 | 15 | 80 |
| b | 2 | 1 | 0.5 | 25 | 0 | 75 |
| c | 1 | 1 | 0.5 | 54 | 0 | 46 |
| d | 1 | 0.5 | 0.25 | 5 | 14 | 55 |
| e | 2 | 2 | 1 | 69 | 0 | 31 |
| f | 3 | 3 | 1.5 | 99 | 0 | 1 |

EXAMPLE 3

Preparation of 3-Nitroxethylphenil Ester of the 2-Acetoxybenzoic Acid by Nitration With Steaming Nitric Acid, in the Presence of Acetic Anhydride, of 3-Hydroxymethylphenyl Ester of the 2-Acetoxybenzoic Acid A solution of steaming nitric acid (1.44 g, 22.8 mmoles), acetic anhydride, (2.33 g, 22.8 mmoles) in dichloromethane (25 ml) is cooled at 0° C. and under stirring added in 1 hour, in nitrogen atmosphere, with a 3-hydroxymethylphenyl ester solution of the 2-acetoxybenzoic acid (6 g, 20.7 mmoles) in 25 ml of dichloromethane. The mixture is heated up to 20° C. in one hour and then diluted with dichloromethane (50 ml) and poured into water and ice (100 g). The organic phase is separated, washed with water, anhydrified with sodium sulphate and the solvent evaporated under vacuum. The residue is crystallized from isopropanol and 3-nitroxymethylphenyl ester of the 2-acetoxybenzoic acid (5.6 g, 17 mmoles, yield 82%) is obtained.

EXAMPLE 4

Preparation of 3-Nitroxymethylphenyl Ester of the 2-Acetoxybenzoic Acid by Nitration With Steaming Nitric Acid, in the Presence of Acetic Anhydride, of 3-Hydroxymethylphenyl Ester of the 2-Acetoxybenzoic Acid (Acetic Anhydride Mixed With Hydroxyester)

A solution of steaming nitric acid (1.44 g, 22.8 mmoles), in dichloromethane (25 ml) is cooled at 0° C. and added in 1 hour, under stirring and in nitrogen atmosphere, with a solution of 3-hydroxymethylphenyl ester of the 2-acetoxybenzoic acid (6 g, 20.7 mmoles) and acetic anhydride (2.33 g, 22.8 mmoles) in 25 ml of dichloromethane. The mixture is heated up to 20° C. in one hour and then diluted with dichloromethane (50 ml) and poured into water and ice (100 g). The organic phase is separated, washed with water, anhydrified with sodium shulphate and the solvent evaporated under vacuum. The residue is crystallized frown isopropanol to give 3-nitroxymethylphenyl ester of the 2-acetoxybenzoic acid (6.42 g, 19.5 mmoles, yield 94%).

EXAMPLE 5

Preparation of 3-Nitroxymethylphenyl Ester of the 2-Acetoxybenzoic Acid by Nitration With Steaming Nitric Acid, in the Presence of Methansulphonic Acid, of 3-Hydroxymethylphenyl Ester of the 2-Acetoxybenzoic Acid A steaming nitric acid solution (1.44 g, 22.8 mmoles) and methansulphonic acid (2.55 g, 22.8 mmoles) in dichloromethane (25 ml) is cooled at 0° C. and under stirring added in 1 hour, in nitrogen atmosphere, with a 3-hydroxymethylphenyl ester solution of the 2-acetoxybenzoic acid (6 g, 20.7 mmoles) in 25 ml of dichloromethane. The mixture is diluted with dichloromethane (50 ml) and poured into water and ice (100 g). The organic phase is separated, washed with water, anhydrified with sodium sulphate and the, solvent evaporated under vacuum. The residue is crystallized from isopropanol to give 3-nitroxymethylphenyl ester of the 2-acetoxybenzoic acid (2.73 g, 8.29 mmoles, yield 40%).

EXAMPLE 6

Preparation of 3-Nitroxymethylphenyl Ester of 2-Acetoxybenzoic Acid by Nitration With Steaming Nitric Acid, in the Presence of Acetic Anhydride, of 3-Hydroxymethylphenyl Ester of the 2-Acetoxybenzoic Acid A steaming nitric acid solution (990 mg, 15.2 mmoles), acetic anhydride (1.55 g, 15.2 mmoles) in dichloromethane (25 ml) is cooled at 0° C. and, under stirring, added in 1 hour, under nitrogen atmosphere, with a solution of 3-hydroxymethylphenyl ester of the 2-acetoxybenzoic acid (4 g, 13.8 mmoles) in 25 ml of dichloromethane. The mixture is heated in one hour up to 20° C. and then diluted with dichloromethane (50 ml) and poured into water and ice (100 g). The organic phase is separated, washed with water, anhydrified with sodium sulphate and the solvent evaporated under vacuum. The residue is crystallized from isoprotanol to give 3-nitroxymethylphenyl ester of the 2-acetoxybenzoic acid (4.1 g, 12.28 mmoles, yield 89%).

What is claimed is:

1. A process for obtaining compounds of formula (I):

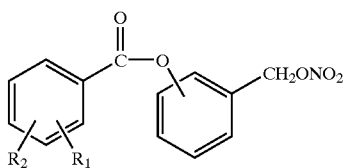
(I)

wherein:

$R_1$ is the $OCOR_3$ group; wherein $R_3$ is methyl, ethyl or linear or branched $C_3$–$C_5$ alkyl or saturated heterocyclic ring having 5 atoms, containing heteroatoms independently selected between O and N;

$R_2$ is hydrogen, halogen, linear or branched when possible $C_1$–$C_4$ alkyl, linear or branched when possible $C_1$–$C_4$ alkoxyl; linear or branched when possible $C_1$–$C_4$ perfluoroalkyl; mono- or di-($C_1$–$C_4$)alkylamino;

said process comprising the following steps:

a) reaction between an halide and a salicylic acid derivative formula (I-A)

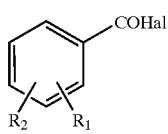
(I-A)

wherein Hal=Cl, Br, and $R_1$ and $R_2$ have the above indicated meaning, with hydroxybenzylalcohol in the presence of a base in an organic solvent, or in a mixture of water with an organic solvent miscible or immiscible in water, to give the compound (I-B) having the following formula:

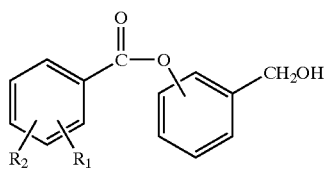
(I-B)

wherein $R_1$ and $R_2$ are as above defined;

b) nitration of the compound (I-B) in anhydrous conditions, in an inert organic solvent, by a mixture formed by steaming nitric acid with an inorganic acid different from nitric acid, or with an organic acid, or with an anhydride of one or two organic acids to give the nitroxy derivative formula (I).

c) recovery of the final product by adding water to the organic phase, separating the phases, drying and evaporating the organic phase.

2. A process according to claim 1, wherein in step a) the base is an inorganic or organic base.

3. A process according to claim 1, wherein in step a) the organic solvents are $C_1$–$C_4$ aliphatic alcohols; aromatic hydrocarbons, aliphatic esters, chlorinated organic solvents, aliphatic and cycloaliphatic ketones.

4. A process according to claim 1, wherein in step a) the reaction is carried out at a temperature in the range −20° C. and +50° C. by using, with respect to the hydroxybenzylalcohol moles under reaction, an amount by moles respectively of acid halide (I-A) in the range between 1 and 2.

5. A process according to claim 1, wherein step b) nitration is carried out at a temperature in the range −20° C. and +40° C. and the amount by moles of nitric acid is in a ratio between 1 and 6, with respect to the moles of the compound (I-B), the amount by moles of inorganic acid different from nitric acid, or of organic acid or of organic anhydride as above defined, is in a ratio comprised between 0.5 and 6, preferably between 1 and 3 with respect to the moles of the compound (I-B).

6. A process according to claim 5, wherein nitration is carried out in the presence of an anhydride, which is premixed with the hydroxyester (I-B) and the resulting mixture added to the nitric acid solution in the inert organic solvent.

7. A process according to claim 6, wherein anhydride is acetic anhydride.

8. A process according to claim 1, wherein in formula (I) $R_1$ is acetoxy and it is in ortho position with respect to the carboxylic group, $R_2$ is hydrogen; the oxygen of the ester group is bound to the aromatic ring substituted with the (nitroxy)methylene group in ortho, meta or para position with respect to the (nitroxy)methylene group.

9. The process according to claim 4, wherein the amount by moles of the acid halide is from 1.2 and 1.5 and the base between 0.5 and 2.

* * * * *